(12) United States Patent
Bidle et al.

(10) Patent No.: US 8,557,514 B2
(45) Date of Patent: Oct. 15, 2013

(54) METHODS FOR OBTAINING BIOACTIVE COMPOUNDS FROM PHYTOPLANKTON

(75) Inventors: Kay Daniel Bidle, Lawrenceville, NJ (US); Assaf Vardi, Haifa (IL); Benjamin A. S. Van Mooy, Falmouth, MA (US); Helen F. Fredricks, Rochester, MA (US); Liti Haramaty, East Brunswick, NJ (US)

(73) Assignees: Woods Hole Oceanographic Institution, Woods Hole, MA (US); Rutgers, The State University of New Jersey, New Brunswick, NJ (US)

( * ) Notice: Subject to any disclaimer, the term of this patent is extended or adjusted under 35 U.S.C. 154(b) by 908 days.

(21) Appl. No.: 12/459,826

(22) Filed: Jul. 7, 2009

(65) Prior Publication Data
US 2010/0145084 A1  Jun. 10, 2010

Related U.S. Application Data

(60) Provisional application No. 61/078,529, filed on Jul. 7, 2008.

(51) Int. Cl.
*C11C 1/00* (2006.01)
*C12P 7/00* (2006.01)
*C12P 7/64* (2006.01)
*C12Q 1/70* (2006.01)

(52) U.S. Cl.
USPC ............... 435/5; 435/132; 435/134; 435/271

(58) Field of Classification Search
None
See application file for complete search history.

(56) References Cited

U.S. PATENT DOCUMENTS

| | | | |
|---|---|---|---|
| 5,821,072 A | 10/1998 | Schwartz et al. | |
| 6,793,945 B2 | 9/2004 | Bathurst et al. | |
| 2002/0110608 A1* | 8/2002 | Bathurst et al. | 424/757 |
| 2010/0145084 A1 | 6/2010 | Bidle et al. | |
| 2011/0129851 A1 | 6/2011 | Bidle et al. | |

FOREIGN PATENT DOCUMENTS

WO   WO 2011/057132   5/2011

OTHER PUBLICATIONS

Allen et al., Proteomic analysis of the EhV-86 virion (abstract) Proteome Sci 6:11 (2008) [retrieved Mar. 5, 2012] Retrieved from Internet < URL: http://www.ncbi.nlm.nih.gov/pubmed?term=allen%20proteome%20sci.%206.

Allen et al., Use of microarrays to assess viral diversity: from genotype to phenotype. Environmental Microbiology 9(4): 971-982 (2007).
Allen, Locus-Specific Gene Expression Pattern Suggests a Unique Propagation Strategy for a Giant Algal Virus. J. Virology 80(15) 7699-7705 (2006).
Bidle et al. Cell death in planktonic, photosynthetic microorganisms. Nature Rev. Microbiol. 2:643-655 (2004).
Bidle et al., Iron starvation and cultrue age activate metacaspases and programmed cell death in the marine diatom *Thalassiosira pseudonana*. (abstract) Eukaryot Cell (2): 223-36 (2008) [retrieved Mar. 5, 2012] Retrieved from Internet < URL: http://www.ncbi.nlm.nih.gov/pubmed?term=bidle%20bender%20eukaryotic%20cell.
Bidle et al., Viral activation and recruitment of metacaspases in the unicellular coccolithophore, *Emiliania huxleyi*. PNAS 104(14):6049-6054, Apr. 2007.
Brügger et al., The HIV lipidome: A raft with an unusual composition. Proc. Natl. Acad. Sci. USA. 103(8): 2641-2646 (2006).
Brussaard et al, Virus-like particles in a summer bloom of *Emiliana huxleyi* in the North Sea. Aquat Microb Ecol 10: 105-113 (996).
Brussaard, Viral Control of Phytoplankton Populations—a Review. J. Eukaryotic Microbiol. 51(2): 125-138 (2004).
Evans, C. et al "Changes in *Emiliania huxleyi* fatty acid profiles during infection with *E-huxleyi* virus 86: physiological and ecological implications" Aquatic Microbial Ecology 55(3): 219-228 (2009).
Fuhrman, Marine viruses and their biogeochemical and ecologicial effecfts. Nature vol. 399, 541-548 (1999).
Grassme et al., Host defense against *Pseudomonas aeruginosa* requires ceramide-rich membrane rafts. Nat Med 9(3): 322-330 (2003).
Han, G. et al "Expression of a novel marine viral single-chain serine palmitoyltransferase and construction of yeast and mammalian single-chain chimera" The Journal of Biological Chemistry 281(52): 39935-39942 (2006).
Khuruna et al., Apoptosis in plant disease response : A close encounter of the pathogen kind. Current Science, 88 (5) 740-752 (2005).
Koga et al., Cerebrosides A and C, Sphingolipid Elicitors of Hypersensitive Cell Death and Phytoalexin Accumulation in Rice Plants. J. Biol. Chem. 273, 31985 (1998).
Lynch et al. An introduction to plant sphingolipids and a review of recent advances in understanding their metabolism and function *New Phytol.* 161, 677 (2004).
Molinski et al., Drug development from marine natural products. Nature Reviews/Drug Discovery vol. 8, 69-85 (2009).
Parker et al., Genomic Insights into Marine Microalgae Annu. Rev. 42: 619-645 (2008).
Reiter et al., Viral killer toxins induce caspase-mediated apoptosis in yeast. JCB 168(3) 353-358 (2005).

(Continued)

*Primary Examiner* — Debbie K Ware
(74) *Attorney, Agent, or Firm* — Ropes & Gray LLP; David P. Halstead; David P. Pleynet (57) ABSTRACT

Phytoplankton represent a potential source of bioactive compounds. The present disclosure provides, inter alia, methods for identifying glycerolipids and apoptosis-inducing sphingosine-like lipids from virally-infected phytoplankton.

18 Claims, 6 Drawing Sheets

(56) References Cited

OTHER PUBLICATIONS

Richier et al., Light-Dependent Transcriptional Regulation of Genes of Biogeochemical Interest in the Dipliod and Haploid Life Cycle Stages of *Emiliania huxleyi*. Applied and Enviornmental Microbiology 75(10): 3366-3369 (2009).

Sakamoto et al., Host sphingolipid biosynthesis as a target for hepatitis C virus therapy. Nat Chem Biol 1(6): 333-337 (2005).

Schroeder et al., Coccolithovirus (Phycodnaviridae): Characterization of a new large dsDNA algal virus that infects *Emiliana huxleyi*. (abstract) Archives of Virology 147(9) [retreived Mar. 5, 2012] Retrieved from Internet < URL: http://www.springerlink.com/content/29uj6cb2qbhv3ugb/abstract/?target=print.

Sturt et al., Intact polar membrane lipids in prokaryotes and sediments deciphered by high-performance liquid chromatography/eletrospray ioization multistage mass spectrometry—new biomarkers for bioeochemistry and microbial ecology. Rapid Communications in Mass Spectrometry 18: 617-628 (2004).

Suttle, Marine viruses—major players in the global ecosystem. Nature Reviews Microbiology 5: 801-812 (2007).

Suttle, Viruses in the sea. Nature 15: 356-361(2005).

Van Mooy et al., Phytoplakton in the ocean use non-phosphorus lipids in response to phosphorus scarcity. Nature 458: 69-72 (2009).

Vardi et al., A Diatom Gene Regulating Nitric-Oxide Signaling and Suscepilbity to Diatom-Derived Aldehydes. Curr. Biol. 18: 895-899 (2008).

Vardi et al., A Stress Surveillance System Based on Calcium and Nitric Oxide in Marine Diatoms Aldehydes released by marine diatoms trigger intracellular calcium transients and nitric oxide generation, which results in cell death. Plos Biology 4(3): 411-419 (2006).

Vardi et al., Programmed cell death of the dinoflagellate *Peridinium gatunense* is mediated by $CO_2$ limitation and oxidative stress. Curr. Biol. 9(18) 1061-1064 (1999).

Vardi, A. et al. "Viral Sphingolipids Biomimic Infection via Induction of Coccolithophores Programmed Cell Death" (Abstract) In: 3rd Annual meeting of the SCOR Working Group on the Role of Viruses in Marine Ecosystems. May 14-16, 2009. University of Delaware. Newark, The United States of America. p. 38[retrieved Dec. 7, 2010]. Retrieved from Internet < URL: http://scor-viral-ecology.dbi.udel.edu/SCOR2009_meetingsprogram.pdf.

Vardi, A. et al. "Virally-Induced Sphingolipids Regulate Host Cell Fate in the Marine Coccolithophore, *Emiliania huxleyi*" (Abstract) in: ASLO Aquatic Sciences Meeting 2009. Jan. 25-30, 2009. Centre de Congres Acropolis. Nice, France. [retrieved Dec. 7, 2010]. Retrieved from Internet < URL: http://www.sgmeet.com/aslo/nice2009/viewabstract2.asp?AbstractID=4839>.

Vaulot et al., The diversity of small eukaryotic phytoplankton (< 3µm) in marine ecosystems. FEMS Microbiol Rev 32: 795-820 (2008).

Wilson et al., Complete Genome Sequence and Lytic Phase Transcription Profile of a Coccolithovirus. Science 309: 1090-1092 (2005).

Koopman et al., "Annexin V for flow cytometric detection of phosphatidylserine expression on B cells undergoing apoptosis", Blood 84(5):1415-1420 (1994).

Lowe et al. " p53-dependent apoptosis modulates the cytotoxicity of anticancer agents", Cell 74:957-967 (1993).

Van Mooy et al., "Sulfolipids dramatically decrease phosphorus demand by picocyanobacteria in oligotrophic marine", PNAS 103(23):8607-8612 (2006).

Vardi et al., "Viral glycosphingolipids induce lytic infection and cell death in marine phytoplankton", Science 326(5954):861-865 (2009).

\* cited by examiner

METHODS FOR OBTAINING BIOACTIVE COMPOUNDS FROM PHYTOPLANKTON

RELATED APPLICATIONS

This application claims the benefit of U.S. Provisional Application No. 61/078,529, filed on Jul. 7, 2008, the specification of which is incorporated herein in its entirety.

BACKGROUND

Identification of drugs that modulate apoptosis is a major goal of the pharmaceutical and biotechnology industries. Apoptosis, or programmed cell death, serves many purposes in cell populations. Termination of damaged, stressed or infected cells conserves resources for healthy cells and may help to prevent spread of infection. In multicellular organisms, a changing environment often leads to cycles of cell proliferation or death, depending on the needs of the organism. Similarly, during development of multicellular organisms, excess cells are produced but later removed by apoptosis. Finally, the importance of apoptosis in the health of an organism is underscored by the consequences of excess apoptosis or lack of apoptosis. In humans, excess apoptosis is linked to autoimmune and neurodegenerative diseases, while a lack of apoptosis contributes to the uncontrolled growth of cancerous cells.

Because apoptosis is induced by signals external or internal to the cell, it is contemplated that identification and purification of select signals could provide useful compositions for modulating apoptosis in cell populations, multicellular organisms, and in human disease. Accordingly, there remains a need for identifying compositions that induce or inhibit apoptosis.

Marine organisms provide a vast source of natural products for use in pharmaceutical and biomedical applications. Many novel compounds have been identified in marine invertebrates, including potent anti-tumor and anti-mitotic compounds currently in clinical trials. Marine microorganisms, which represent an estimated 90% of the biomass in the ocean (Suttle, Nature Reviews Microbiology, Vol. 5, 801-812 (2007)), are also potential sources of novel chemical structures.

SUMMARY OF INVENTION

The present disclosure describes methods for isolating bioactive compounds from phytoplankton. The methods are based on the interaction observed between phytoplankton and lytic viruses, wherein viral infection of the phytoplankton induces production of lipids. Lipids may be sphingosine-like lipids and/or glycerolipids.

One aspect of the present disclosure provides a method for isolating one or more apoptosis-inducing lipids, such as sphingosine-like lipids, comprising: (a) obtaining a sample of one or more lipids from a virally-infected phytoplankton; (b) contacting a target cell with the sample; (c) assaying the target cell for apoptosis-associated activity in the presence of the sample; wherein apoptosis-associated activity in the target cell indicates that the sample comprises one or more apoptosis-inducing lipids.

The phytoplankton may be coccolithophores, such as *E. huxleyi*, and the virus may be a coccolithovirus, such as EhV86. The method may further comprise isolating the one or more apoptosis-inhibiting lipids from the sample, e.g., by chromatography, for example by HPLC, and may also comprise analyzing the one or more apoptosis-inducing lipids by mass spectrometry.

The target cells used in the present methods may be prokaryotic cells or eukaryotic cells. In various embodiments, the target cells may be phytoplankton cells, such as coccolithophores, e.g., *E. huxleyi*. A eukaryotic cell may be a plant cell or an animal cell, such as mammalian cell, e.g., a human cell.

The methods of the present disclosure also feature assays for apoptosis-associated activity. Apoptosis-associated activity may be apoptosis, a decrease in photosynthetic efficiency, an increase in expression of a caspase gene and/or an increase in caspase activity. Apoptosis-associated activity may also be cell shrinkage, DNA fragmentation, or membrane blebbing.

Sphingosine-like lipids, such as glycosylated sphingosine-like lipids, may induce apoptosis in cells. In some embodiments, glycosylated sphingosine-like lipids may be viral glycosylated sphingosine-like lipids.

The present disclosure also contemplates methods of manufacturing lipids using phytoplankton. In some embodiments, a method of manufacturing one or more sphingosine-like lipids may comprise infecting phytoplankton with a virus, culturing the infected phytoplankton, and isolating one or more sphingosine-like lipids, such as apoptosis-inducing sphingosine-like lipids, from the infected phytoplankton. In other embodiments, a method of manufacturing one or more glycerolipids may comprise infecting phytoplankton with a virus, culturing the infected phytoplankton, and isolating the one or more glycerolipids from the infected phytoplankton. The one or more glycerolipids may be capable of inhibiting apoptosis, such as viral-mediated apoptosis.

Another aspect of the present disclosure provides a method for isolating one or more lipids, such as glycerolipids, capable of inhibiting viral-mediated apoptosis, e.g., by obtaining a sample of one or more lipids from a virally-infected phytoplankton; contacting a target cell with the sample; and assaying the target cell for apoptosis-associated activity in the presence of the sample and in the presence of a stimulus that induces apoptosis in the target cell in the absence of the sample, wherein a decrease in apoptosis-associated activity in the target cell relative to the activity in the absence of the sample indicates that the sample comprises one or more lipids capable of inhibiting apoptosis. In some embodiments, the stimulus is a virus that infects the cell and induces apoptosis. In various embodiments, cell may be contacted with the sample before the virus infects the cell, or after the virus infects the cell.

The phytoplankton may be coccolithophores, e.g., *E. huxleyi*, and the virus may be a coccolithovirus, e.g., EhV86. The method may further comprise isolating one or more lipids from the sample, e.g., by chromatography, for example by HPLC, and may also comprise analyzing the one or more lipids by mass spectrometry.

The target cells used in the present methods may be prokaryotic cells or eukaryotic cells. Thus, the target cells may be phytoplankton cells, such as coccolithophores, e.g., *E. huxleyi*. A eukaryotic cell may be a plant cell or an animal cell, such as mammalian cell, and/or a human cell.

The methods of the present disclosure also feature assays for apoptosis-associated activity. Apoptosis-associated activity may be apoptosis, a decrease in photosynthetic efficiency, an increase in expression of a caspase gene and/or an increase in caspase activity. Apoptosis-associated activity may also be cell shrinkage, DNA fragmentation, or membrane blebbing.

BRIEF DESCRIPTION OF DRAWINGS

FIG. 3 shows the biomimicry of viral infection mediated by purified viral GSLs. Viral GSLs were applied to uninfected *E. huxleyi* cells and induced PCD. Dose-dependent induction of cell death in uninfected Ehux374 cells over 72 h by application of purified GSLs (0.06, 0.3, 1.5 µg/mL). Cell abundance (cells $ml^{-1}$; bars) and photochemical quantum yield of photosystem II (Fv/Fm; circles) (FIG. 3A), and in vivo caspase activity (measured by flow cytometry) (FIG. 3B). Cytograph plots represent the fluorescence distribution for CaspACE-stained samples in respective treatments after 48 h. The percentage of positively stained cells is given in each panel. Dashed line represents the threshold fluorescence above which cells are positively stained, determined by unstained controls of each treatment. Images of GSL-treated cultures exhibited massive cell lysis after 72 h (FIG. 3C). The percentage of SYTOX positive cells is given for 72 h treatments (inset) and serves as a proxy for dying cells. Control treatments consisted of DMSO (solvent) and the membrane phospholipid phosphatidylglycerol (PG).

FIG. 4 is a detailed profile of lipids conferring resistance to viral infection. A dramatic induction of the lipids (called 802 lipids) (>100 fold above baseline) is clearly observed only in sensitive strain Ehux374 during the onset of lytic phase. Concomitant with the induction of 802, a major reduction in the lipids (called 830 lipids) occurred during the lytic phase.

FIG. 6A shows cell growth of Ehux374 in the presence or absence of EhV86, with or without the 802 lipid. FIG. 6B shows the photosynthetic efficiency, as measured by photochemical quantum yield of photosystem II (Fv/Fm).

DETAILED DESCRIPTION

A. Overview

The present disclosure describes methods for the identification and production of sphingosine-like lipids, such as sphingosine-like lipids and glycerolipids from a virus-phytoplankton system. Sphingosine-like lipids are amino alcohols acylated by a fatty acid and comprise a fatty acid chain and a sphingosine-like portion. The sphingosine-like lipids induce apoptosis and/or apoptosis-associated activity in cells, while the glycerolipids inhibit viral-mediated apoptosis. Methods disclosed herein make use of the coevolutionary relationship between marine viruses and phytoplankton. Marine viruses that infect and terminate phytoplankton are recognized as a major ecological and evolutionary driving force, shaping community structure and nutrient cycling in the marine environment. The molecular interactions between phytoplankton and viruses are complex, and involve a suite of pathways comprising apoptosis, cell-signaling, cell metabolism, immune response, and lipid biosynthesis.

The molecules generated by this interaction may have potent bioactivities. The molecules produced are in addition to or in excess of what is contained in either the host-phytoplankton or in the viruses that may infect them. The virus induces production of bioactive compounds in the infected phytoplankton, either by recruiting host machinery to generate viral molecules, or by triggering production of host molecules. Thus, the chemical composition of the combined phytoplankton/virus system may change during the course of viral infection.

Infected cells and/or surrounding culture media may be collected during the course of viral infection, and chemical extracts may be prepared. The extracts may contain chemically pure molecules, or mixtures of molecules. In some embodiments of the present disclosure, the lipid composition within the phytoplankton-virus system changes during the course of infection. In particular, a group of sphingosine-like lipids appears within 3.5 hours after infection, and levels of these sphingosine-like lipids rise in concert with apoptosis of the phytoplankton. As described herein, experiments in uninfected cells demonstrate that a preparation of isolated sphingosine-like lipids induces apoptosis in uninfected cells, indicating that the virus-phytoplankton system serves as a platform for producing and/or identifying apoptosis-inducing lipids, such as sphingosine-like lipids.

In other embodiments of the present disclosure, a group of glycerolipids (herein also called the 802 lipids) is generated, e.g., within 45 hours after infection. These glycerolipids tend to appear as a second group of glycerolipids (herein called the 830 lipids) disappears. As described herein, experiments demonstrate that a preparation of the 802 lipids inhibits viral-mediated apoptosis in a population of virus-infected cells. Thus, the virus-phytoplankton system also serves as a platform for producing and/or identifying lipids that inhibit viral-mediated apoptosis of cells.

A sample of lipids may be prepared by removing infected phytoplankton cells, pelleting the cells by centrifugation, and lysing the cells to access the membranes and/or intracellular contents. Fractions of phytoplankton may be enriched for endoplasmic reticulum, reticular body, mitochondria, Golgi apparatus, coccolith-producing compartments, plastids, chloroplasts, nuclei, membranes associated with these organelles, and/or the plasma membrane. Alternately, the sample of lipids may be prepared directly from the lysed cells, without further fractionation.

To identify other lipids that modulate apoptosis, samples of lipids (e.g., containing either sphingosine-like lipids or glycerolipids) extracted from virally-infected phytoplankton may be screened for their ability to induce apoptosis or inhibit apoptosis, such as viral-mediated apoptosis. When desired sphingosine-like lipids or glycerolipids have been identified, the present disclosure contemplates the use of the virus-phytoplankton system for manufacturing the desired lipids. Production of virally-infected phytoplankton may be scaled up, either in an open-pond system or in a bioreactor. Notably, cultured phytoplankton are widely used in the manufacture of food and cosmetics additives and are being further developed for large-scale production of biofuels.

1. Phytoplankton

Phytoplankton include a diverse assemblage of photosynthetic organisms, comprising both prokaryotic cyanobacteria and eukaryotic algae. Among the eukaryotic phytoplankton, the coccolithophores are one of the most abundant classes of unicellular phytoplankton, and often dominate the modern ocean. Coccolithophores belong to the phylum haptophytes, and possess calcium carbonate plates (or scales) called coccoliths. They are normally found in the surface euphotic zone of the ocean, and can be cultured in the laboratory setting.

*Emiliana huxleyi* is the most abundant and cosmopolitan species within the coccolithophores. *E. huxleyi* grow into massive annual blooms and die by metacaspase-mediated mechanisms (Bidle et al., PNAS 104(14): 6049-6054 (2007)). Generally, caspase-mediated death of phytoplankton may be a mechanism of programmed cell death in response to bacterial or viral infection, environmental stress or DNA damage from reactive oxygen species or UV exposure (Bidle and Falkowski. Nature Rev. Microbiol. 2:643-655 (2004), Parker et al., Ann. Rev. Genet. 42:619-45 (2008)).

In one aspect of the present disclosure, the phytoplankton used in the virus-phytoplankton system belong to the haptophyte phylum. Haptophytes typically have two slightly unequal flagella, and a unique organelle called a haptonema, which resembles a flagellum but differs in the arrangement of microtubules and in its use. The mitochondria have tubular cristae. Other well-known examples of haptophytes include *Pavlova lutheri* and *Isochysis galbana* which are used as a feed source for aquaculture, and coccolithophores, which are the most abundant of the haptophytes. The phytoplankton of the present methods may be coccolithophores, and further, may be *E. huxleyi*. The *E. huxleyi* may be any suitable virus-sensitive strain such as one of *E. huxleyi* strains 374, 92F, 1516, CCMP 1516, EH2, S. Africa, L, or Bloom (Allen et al., Environmental Microbiology, 9(4) 971-982 (2007)).

2. Marine Viruses

Marine viruses are the most abundant biological entities in the ocean. The impact of viral infection is enormous. By some estimates, viral infection of marine microorganisms eliminates 20% of the ocean's biomass per day. Thus, viruses may serve as a powerful ecological and evolutionary driving force for biodiversity in the ocean (Suttle, Nature Reviews Microbiology, Vol. 5, 801-812 (2007); Fuhrman, Nature 399:541-548 (1999)).

Viral killing of phytoplankton has been confirmed in laboratory experiments with lytic viruses, which direct phytoplankton hosts to produce progeny and eventually lyse the host to release progeny viruses. Studies suggest that the virus induces a cascade of metacaspase signaling, eventually leading to programmed cell death, which may act as a defense against massive viral infection and demise of the population. Activation of caspase-linked activity after viral infection has been identified in several phytoplankton species, including *E. huxleyi* (Bidle et al., PNAS 104(14): 6049-6054 (2007)). Metacaspase genes or caspase-like homologues have also been identified in the genomes of many other marine algae, suggesting that viral induction of metacaspases and programmed cell death may be a conserved mechanism in phytoplankton (Bidle and Falkowski. Nature Rev. Microbiol. 2:643-655 (2004); Parker et al., Ann. Rev. Genet. 42:619-45 (2008)).

Marine viruses may be specific to the host phytoplankton. Accordingly, in one aspect of the present disclosure, the virus component in the virus-phytoplankton system is a Phycodnaviridae, a family that infects marine or freshwater eukaryotic algae. The virus may be a coccolithovirus (Wilson et al., Science, 309: 1090-1092 (2005)). The coccolithovirus may be EhV86, or other strains capable of infecting *E. huxleyi*. Suitable strains include EhV1, EhV-84, EhV-88, EhV-163, EhV-201, EhV-202, EhV-203, EhV-204, EhV-205, EhV-206, EhV-207, EhV-208, EhV-209, EhV-V2 (Allen et al., Environmental Microbiology, 9(4) 971-982 (2007)).

In the laboratory setting, viral particles are purified from a lysate of cells infected with the virus. For example, EhV86 may be first propagated by using batch cultures of *E. huxleyi* strain 374 (Ehux374) grown in f/2 (minus Si) at 18° C. in 14 hour: 10 hour light-dark illumination. Once clearing of the host cell culture is observed, virus-containing cell lysates are centrifuged and passed through 0.4 µm polycarbonate filters to remove cellular and particulate debris before infection. Viral lysates may be stored at 4° C. To infect fresh *E. huxleyi* cells, the viral lysates are added to exponentially growing ($1.5 \times 10^6$ mL$^{-1}$) cells. In some embodiments, 1 mL of lysate may be added to 100 mL of cells. Inoculated cultures may be occasionally agitated to encourage adsorption of virus to cells (Allen et al., Environmental Microbiology, 9(4): 971-982 (2007)). The latent period of a coccolithovirus in *E. huxleyi* is reported to be 12-14 hours, and burst size is 400-1000 infective units per cell (Brussard, J. Eukaryotic Microbiology, 51:2, 125-138, (2004))

*E. huxleyi* has been shown to carry virus-like particles of different size classes in one cell (Brussard, Aquat. Microb. Ecol., 10:105-113, (1996)). EhV86 is not known to infect species other than *E. huxleyi*, but other viruses are known to infect more than one phytoplankton: For example, *M. pusilla* can be infected by a dsDNA virus from the phycodnaviridae family and a dsRNA virus from the reoviridae family (Brussard, J. Eukaryot. Microbiol., 51(2), 125-138, (2004)). Any virus or combination of viruses that infect a phytoplankton of interest can be used in the methods disclosed herein.

B. Lipids

1. Induction of Sphingosine-like Lipids and Glycerolipids

Following infection by virus, the phytoplankton may express viral gene products and/or express host gene products in response to the virus. Gene products may comprise nucleic acids such as DNA or RNA, amino acids, peptides, and/or proteins, any of which may be modified with lipids, sugars, phosphates or other moieties. By varying conditions of growth, such as light, temperature, time, and nutrients, the relative amounts and/or identities of the products generated may be varied.

In some embodiments, viruses induce production of lipids in the phytoplankton host. Expression of these lipids may occur immediately after infection by the virus, or may be observed within a range of 0.1-100 hours post-infection. In some embodiments, a new lipid may occur and/or may be observed at 1, 2 or 4 hours post-infection (Allen, J. Virology, 2006, 80(15) 7699-7705). In other embodiments, viral infection may induce a decrease in the levels of lipids, either viral lipids or host lipids. Thus, the levels of viral lipids, host lipids or a combination of both may increase or decrease over time and peak at or around 3.5 hours, 8 hours, 21 hours, 26.5 hours, 31.5 hours, 45 hours, 52 hours, 56 hours, 69 hours, 75.5 hours, 81.5 hours, and/or 92 hours.

Accordingly, in some embodiments of the present methods, aliquots of the cultures of virally-infected phytoplankton may be removed at intervals, a sample containing lipids may be extracted, and optionally one or more lipids may be further separated on the basis of size, mass, charge, polarity, or other physicochemical properties. The emergence or disappearance of lipids may be assayed at each time point. Molecules which increase or decrease over time may be viral-induced lipids—either of viral origin or host origin—which are suitable for bioactivity screens. Notably, lipids and/or other molecules may appear, disappear, or otherwise change over time in virus-sensitive strains, while corresponding lipids and/or other molecules do not appear, disappear, or otherwise change over time in virus-resistant strains. Comparing the lipid and/or molecule populations over time in virus-sensitive and virus-resistant strains may indicate that the lipids and/or molecules are associated with the virus infection.

In some embodiments, viruses induce production of sphingosine-like lipids in phytoplankton. Sphingolipids, a representative example of which is shown below, are a class of lipids derived from the aliphatic amino alcohol sphingosine.

There are three main types of sphingolipids, differing in their head group R, which may be H, a sugar moiety, or another substituent. Sphingomyelins have a phosphorylcholine or phosphoroethanolamine molecule with an ether linkage to the 1-hydroxy group of a ceramide. Glycosylated sphingolipids are ceramides with one or more sugar residues joined in a β-glycosidic linkage at the 1-hydroxyl position. Cerebrosides have a single glucose or galactose at the 1-hydroxy position. Sulfatides are sulfated cerebrosides. Gangliosides have at least three sugars, one of which must be sialic acid. These compounds play important roles in signal transmission and cell recognition in many organisms. Sphingolipids may play a role in protecting cells by forming a mechanically stable and chemically resistant outer leaflet of the plasma membrane lipid bilayer. In addition, simple sphingolipid metabolites, such as ceramide and sphingosine-1-phosphate, have been shown to be important mediators in the signaling cascades involved in apoptosis, proliferation, and stress responses.

Sphingosine-like lipids, as the term is used herein, include sphingolipids as well as variant compounds in which either the fatty acid portion (i.e., corresponding to the C-17 unsaturated acyl group in the structure depicted above) or the sphingosine portion (i.e., corresponding to the unsaturated C-18 amino diol in the structure depicted above) is altered, e.g., by shortening or lengthening the alkyl chain, varying the number and/or position of unsaturated bonds, substituting the alkyl chain with substituents such as hydroxyl groups, etc., but generally share the overall structural characteristics of having a substantially linear polyol-amine chain in which the amine is acylated by a fatty acid. In certain embodiments, the sphingosine-like portion may be glycosylated, e.g., with one or more sugar residues, such as a glucose or galactose residue, as is commonly seen in cerebrosides, or may be unglycosylated, e.g., bearing an unmodified primary alcohol (e.g., corresponding to R=H in the structure depicted above).

Notably, viruses contain homologues to sphingolipid genes. In the coccolithovirus EhV86, there are at least four genes involved in sphingolipid biosynthesis, encoding sterol desaturase, serine palmitoyltransferase, transmembrane fatty acid elongation protein, lipid phosphate phosphatase, and a two additional genes encoding desaturases (Wilson et al., Science 209, 1090 (2005)). Without wishing to be bound by any theory, in one model of virus-phytoplankton interaction, viral sphingosine-like lipids induce apoptosis in infected phytoplankton.

Consistent with this hypothesis, novel polar membrane lipids appear and increase after viral infection of $E.\ huxleyi$. As disclosed herein, the lipids are glycosylated sphingosine-like lipids, and yield fragmentation ions that indicate an origin from the intermediate compound myristoyl-CoA. This origin is consistent with viral-directed synthesis of glycosylated sphingosine-like lipids, as the host phytoplankton produce palmitoyl glycosylated sphingosine-like lipids. Notably, the myristoyl GSLs are present in infected, virus-sensitive strains, but not in virus-resistant strains.

In certain embodiments, a group of glycerolipids is produced after viral infection of phytoplankton. In certain such embodiments, these glycerolipids (herein called 802 lipids) increase concomitantly with a decrease in a second group of glycerolipids (herein called the 830 lipids). The 802 lipids, when isolated and added to a culture of newly-infected phytoplankton, lead to prolonged survival of virus-infected cells. Glycerolipids, like sphingosine-like lipids, are second messengers that may be involved in signaling cascades involving apoptosis, proliferation, and stress responses.

2. Isolation of Lipids

As described above, lipids may be extracted and monitored over the course of viral infection. Changes in lipid dynamics, such as the emergence of new sphingosine-like lipids, can be observed by isolating lipids or pools of lipids within a sample. Such lipids may be extracted using a Bligh-Dyer method, or a variation thereof, such that all lipids in a phytoplankton cell lysate are extracted in solvents methanol, dichloromethane, and phosphate buffer. Then, the extracted lipid sample may be further separated by chromatography, such as high performance liquid chromatography (HPLC), in order to separate lipids (or pools of lipids) according to their hydrophobicity, size, charge, solubility in a given solvent, adsorption onto stationary phase, and/or other structural properties. Mass spectrometry (MS) analysis may also be used to elucidate the structure and chemical properties of unknown compounds. Thus, for a collection of lipid samples gathered over the time course of viral infection, a lipid profile may be generated, wherein levels of lipids or groups of lipids are monitored. As described above, the lipid profile may change over time, and new lipids, such as sphingosine-like lipids or glycerolipids, may be identified.

3. Screening of Lipids for Apoptosis-inducing Activity

Initially, an isolated fraction containing a sphingosine-like lipid or glycerolipid may be tested for bioactivity, such as apoptosis-associated activity. Apoptosis, the process of programmed cell death (PCD), or cell suicide, is a response to inductive signals originating either external or internal to the cell, which trigger an organized cascade of biochemical and cellular changes. Apoptosis-associated activity comprises one or more of these changes, such as apoptosis, cell shrinkage, blebbing of cell membranes, chromatin condensation and fragmentation, formation of apoptotic bodies, expression of caspase genes, increase in caspase activity, and/or expression of genes associated with apoptosis.

In some embodiments, target cells are contacted with fractions containing lipids, such as sphingosine-like lipids, and apoptosis-associated activity is measured. In other embodiments, target cells are contacted with fractions containing lipids, such as glycerolipids, in the presence of a stimulus that induces apoptosis in untreated cells (such as an apoptosis-inducing virus), and inhibition of apoptosis-associated activity is measured. Detection of apoptosis-associated activity may rely on direct observation of morphological changes in cells. Detection may be performed by microscopic, fluorescence-based and biochemical procedures. Electron microscopy and phase contrast microscopy, for example, detect the morphological appearance during apoptosis, such as shrinkage, membrane protuberances, and the presence of micronuclei (Verhaegen et al., European Microscopy and Analysis (1998)).

In other embodiments, apoptosis-associated activity in test cells contacted with lipids is detected in a flow cytometer. Detection of apoptosis in a sample of suspended cells can be performed using a flow cytometer. Here, fluorescence dyes staining DNA are used (Elstein and Zucker, Experimental Cell Research 211, 322-331 (1994)), or a biochemical method is employed in which the process of DNA fragmentation is visualized by incorporation of nucleotides with fluorescent labels (e.g., TUNEL method, Douglas et al., Journal of Immunological Methods 188, 219-228 (1995)). Also, specific fluorescently labelled probes can be used for cell surface molecules. An example of such a probe is fluorescently labelled annexin V (Koopman et al., Blood 84, 5, 1415-1420 (1994)) which binds to phosphatidylserine on the cell surface and thus visualizes the restructuring of the plasma membrane in the early apoptotic stage. Lastly, one can detect the in vivo activation of caspases, a class of proteases that initiate and execute PCD, through the staining of cells with a fluorescently-labeled (FITC) broad spectrum caspsae inhibitor (z-VAD-FMK). (Bidle and Bender, Eukaryotic Cell 7:223-236 (2008); Bidle et al., Proc. Natl. Acad. Sci. USA 104: 6049-6054 (2007)). However, flow-cytometric methods for the measurement of apoptosis typically require calibration of the method and the system. In addition, a high number of cells (approx. $10^6$) is beneficial for analysis.

Other methods for the detection of apoptosis may require the destruction of all test cells in a sample and the gel-electrophoretic or biochemical detection of DNA fragmentation (Leist et al., The Journal of Immunology 153, 1778-1788 (1994)). These biochemical methods are procedures with several steps in which several reagents are used. This results in a very long time of analysis of up to 6 hours. In addition, several hundred cells are typically used for one analysis.

Detection of apoptosis may also depend on indirect measurements, such as photosynthetic efficiency in phytoplankton. Phytoplankton undergoing apoptosis show a marked reduction in photosynthetic efficiency.

In some embodiments, screens for apoptosis-associated activity may be performed in cell-based assays. The use of genetically-engineered cells, including bacteria, fungi, insect, marine microorganisms, plant cells, and animal cells, is also amenable to high throughput screening (HTS) and automated protocols. Cell-based assays may require that a test compound modulate the expression, binding or activity of a target inside the cell, in such a way that changes to the target are measurable.

In some embodiments, the target cells used in an assay system come from the organism(s) in which a bioactive compound will be used. Thus, target cells may be prokaryotic cells or eukaryotic cells. Cells may be phytoplankton cells, e.g., coccolithophores, such as E. huxleyi. Cells may also be plant or animal cells, such as mammalian cells. Cells may be human cells. In some embodiments, cells may be genetically altered to trigger a specific output (e.g., a fluorescent signal) in the presence of a bioactive compound.

4. Apoptosis in Target Cells

Lipids which induce apoptosis in target cells may prove useful in a variety of settings. In some embodiments, target cells belong to organisms that attach to a surface in contact with water for a period of time. For example, apoptosis-inducing lipids identified using the present methods may be used to induce apoptosis in barnacles, in order to prevent the growth of barnacles on the hulls and/or heating/cooling systems of ships, fishing equipment, and/or offshore oil and gas rigs. Similarly, such lipids may be used to induce apoptosis in algae, diatoms such as *Achnanthes* or *Stauronesis* or bacteria such as *Thiobacilli*, which form a biofilm on surfaces. Biofilms may provide a foundation for growth of seaweed, barnacles, mollusks, seasquirts, sponges, sea anenomes, bryzoans, tube worms, polychaetes, etc. Apoptosis-inducing lipids may be also used to induce apoptosis in any such macroorganisms.

Lipids, such as sphingosine-like lipids identified by the present methods may also be used to induce apoptosis in plant cells. Sphingosine-like lipids such as ceramide are thought to modulates apoptosis in plants (Khuruna et al., Current Science, 88 (5) 740-752 (2005)). Accordingly, sphingosine-like lipids may be screened for apoptosis-inducing activity in specific target plants. For example, a sphingosine-like lipid may be used to kill weeds while leaving crops intact.

Defects in apoptosis form the basis for many diseases in animals. Many cancers, including colorectal cancer, glioma, hepatic cancer, neuroblastoma, leukemias and lymphomata, and prostate cancer have been associated with defects in apoptosis. Autoimmune diseases such as myasthenia gravis and systemic lupus erythematosus, as well as inflammatory diseases such as bronchial asthma, inflammatory intestinal disease, and pulmonary inflammation are also associated with failure of specific immune cells to undergo apoptosis. Finally, some viruses such as HSV, respiratory syncytial virus, HCV, and others may inhibit apoptosis of infected cells. Accordingly, apoptosis-inducing sphingosine-like lipids identified using the present methods may be used to induce apoptosis in cancer cells, lymphocytes that recognize self-peptides, virally-infected cells, or any other cells whose defective apoptosis leads to or contributes to a disease condition.

Similarly, apoptosis-inhibiting lipids identified using the present methods may be used to promote resistance to viral-induced apoptosis. Many viruses, such as dengue virus, EBV, HIV, varicella zoster virus, Abelson virus, are known to promote apoptosis or encode proteins that promote apoptosis. Mechanisms controlling viral-induced apoptosis may be the same mechanisms that are affected in diseases associated with excess apoptosis. Examples of such diseases include, but are not limited to, AIDS, Alzheimer's Disease, ALS, Parkinson's Disease, retinitis pigmentosa, epilepsy, aplastic anemia, myelodysplastic syndrome, lymphocytopenia. Thus, the glycerolipids identified using the present methods may be used to promote resistance to viral-induced apoptosis, or for treating diseases associated with excess apoptosis.

EXAMPLES

The invention now being generally described, it will be more readily understood by reference to the following examples, which are included merely for purposes of illustration of certain embodiments and embodiments of the present invention, and are not intended to limit the invention.

Example 1

Figure 1:
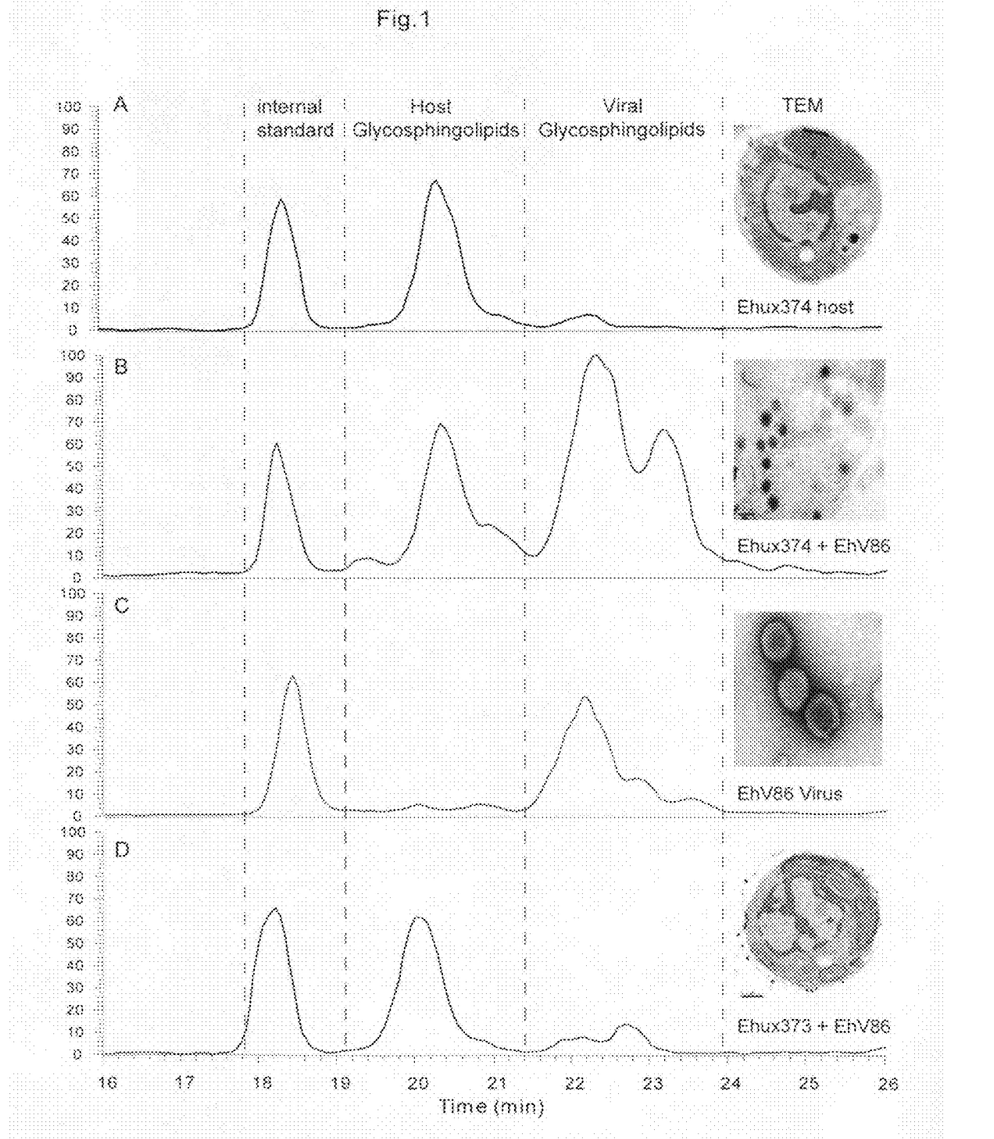
FIG. 1 shows the production of viral glycosylated sphingosine-like lipids (GSLs) in EhV86-infected *E. huxleyi* cells and in purified EhV86 virions. GSL summed ion HPLC/MS chromatograms showing relative abundances of GSLs extracted from susceptible Ehux374 (FIG. 1A), Ehux374 infected with EhV86 52 h post-infection (FIG. 1B), purified EhV86 on a $CsCl_2$ gradient (FIG. 1C), and resistant Ehux373 infected with EhV86 52 h post-infection (FIG. 1D). Peaks were normalized to internal standard. Pictured in the insets are transmission electron microscopy (TEM) images of respective treatments.

Polar Membrane Composition of *E. huxleyi* Strains During a Time Course of Lytic Infection We examined the polar membrane composition of uninfected and EhV86-infected sensitive (Ehux374) and resistant (Ehux373) *E. huxleyi* strains during a time course of lytic infection (e.g. 52 h post-infection). Using high performance liquid chromatography/electrospray ionization mass spectrometry (HPLC/ESI-MS) (Van Mooy et al., Nature, 458: 69-72, (2009)) we compared the lipid composition of uninfected and infected host cells. We detected glycosylated sphingosine-like lipids in uninfected host cells (GSLs) that appeared to be composed of predominantly hydroxylsphingoid bases derived from palmitoyl-CoA (FIG. 1A). These host sphingoid bases are consistent with the expected products of the host SPT which utilizes palmitoyl-CoA and are common in plants (Lynch and Dunn, *New Phytol.* 161, 677 (2004)). However, the lipids from EhV86-infected Ehux374 possessed unique GSLs yielding fragmentation ions that were clearly indicative of multiply-hydroxylated sphingoid bases derived from myristoyl-CoA (FIG. 1B). These sphingoid bases are the expected products of viral serine palmitoyltransferase (SPT), based on the aforementioned preference for myristoyl-CoA. The viral-induced myristoyl-base glycosylated sphingosine-like lipids GSLs were absent in uninfected cells and were unique to lytic viral infection (FIG. 1B). Both resistant and susceptible hosts produced significant concentrations of host palmitoyl GSLs, which were structurally different from the viral myristoyl GSLs (FIG. 1A, D).

To definitively ascertain the origin of the myristoyl GSLs, viruses were purified using a cesium chloride ($CsCl_2$) density gradient and ultracentrifugation. Identical myristoyl GSLs were dominant components of the lipids extracted from purified EhV86 viruses. Furthermore, host palmitoyl GSLs were absent in the purified viruses. These observations strongly suggest that the viral GSLs are an inherent and important component of the membranes underlining the capsid layer (FIG. 1C). Transmission electron microscopy (TEM) of infected Ehux374 cells revealed a structural pattern of viral particles within intra cytoplasmic vacuoles (FIG. 1C-*inset*). Similar structures have also been observed in other giant viruses, such as Mimivirus, which produces specialized viral factories and cytoplasmic replication centers (Suzan-Monti et al., PLoS ONE 2, e328 (2007)). Previous proteomic analysis of EhV-86 virion determined that 23 of a total of 28 proteins are predicted to be membrane proteins (Allen et al., Proteome Sci. 6 (2008)), corroborating our observations of GSLs and membrane structures. Sphingosine-like lipids such as GSLs are ubiquitous constituents of membrane lipids (e.g., lipid rafts) in eukaryotes. Accumulating data suggest that lipid rafts may be involved in the entry and budding of HIV and Hepatitis C, yet their role is not well understood (Bragger et al., Proc. Natl. Acad. Sci. USA. 103, 2641 (2006), Sakamoto et al., Nat Chem Biol 1, 333 (2005)). While sphingolipids are distributed in some prokaryotes, they have never been found in non-enveloped viral membranes (Bragger et al., Proc. Natl. Acad. Sci. USA. 103, 2641 (2006)).

The dramatic accumulation of viral GSLs in Ehux374 during EhV86 infection was accompanied by a dramatic reduction in cell abundance, severely compromised photosynthetic efficiency (declining to 0.22 after 48 h), and ~30 fold induction in caspase specific activity. The potent induction of this fundamental biochemical PCD marker occurred concomitantly with de novo synthesis of viral GSLs and viral production, both signaling the demise of Ehux374 at the onset of the lytic phase at 25 h post-infection. Basal production of viral GSLs began within the first 3.5 h (FIG. 2D), corroborating gene expression data for the virally encoded SPT as early as 2 h post-infection (Allen et al., J. Virology 80, 7699 (2006)). At an advanced state of infection, caspase specific activity and GSL production reached more than 100 fold the levels seen in uninfected cells or in resistant Ehux373 cells (FIG. 2C, 2D).

In contrast, Ehux373 strain displayed resistance to EhV86 infection, exhibiting slightly better growth than control, uninfected Ehux374 cells (FIG. 2A). Photosynthetic health, cell abundance, and caspase specific activity in infected Ehux373 perfectly paralleled the dynamics of uninfected Ehux373 cells through the course of the experiment (FIG. 2A-C). Only trace levels of viral GSLs were detected in infected Ehux373, likely a signature of the EhV86 inoculum (FIG. 2D and FIG. 1D). Both resistant and susceptible hosts produced significant concentrations of host palmitoyl GSLs, which were structurally different from the virally associated myristoyl GSLs (FIG. 1A, D).

Example 2

Bioactive Potential of Viral Glycosylated Sphingosine-like Lipids

Figure 2:
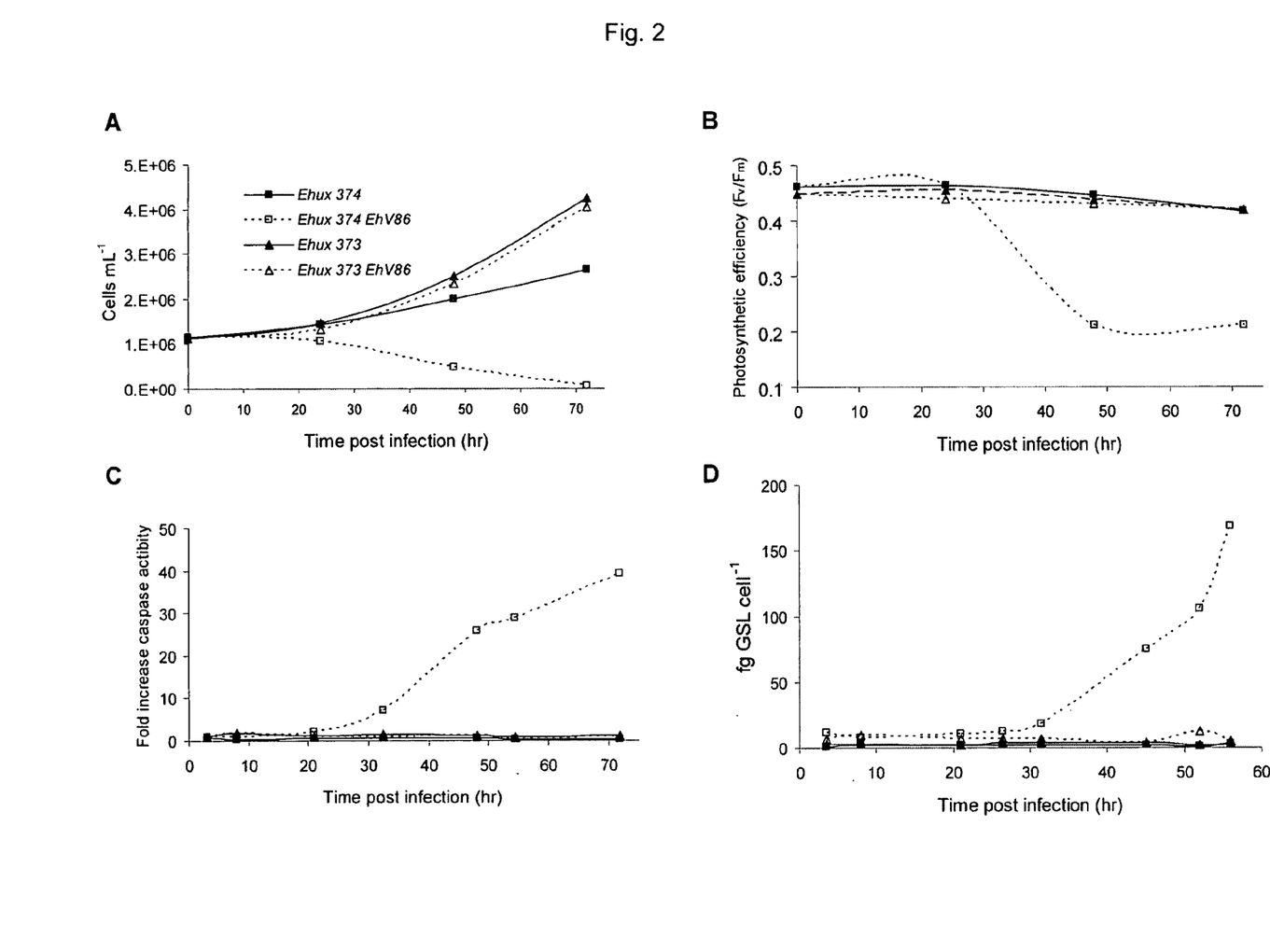
FIG. 2 illustrates the onset of the lytic phase during EhV86 infection is mediated by induction of caspase specific activity and viral GSLs production. Viral infection dynamics of susceptible Ehux374 or resistant Ehux373 strains as monitored by the following parameters: host abundances (FIG. 2A), photochemical quantum yield of photosystem II (Fv/Fm) (FIG. 2B), caspase specific activity (cleavage of IETD-AFC in cell extracts) (FIG. 2C), and de novo synthesis of viral, myristoyl GSLs (FIG. 2D).
Figure 3:
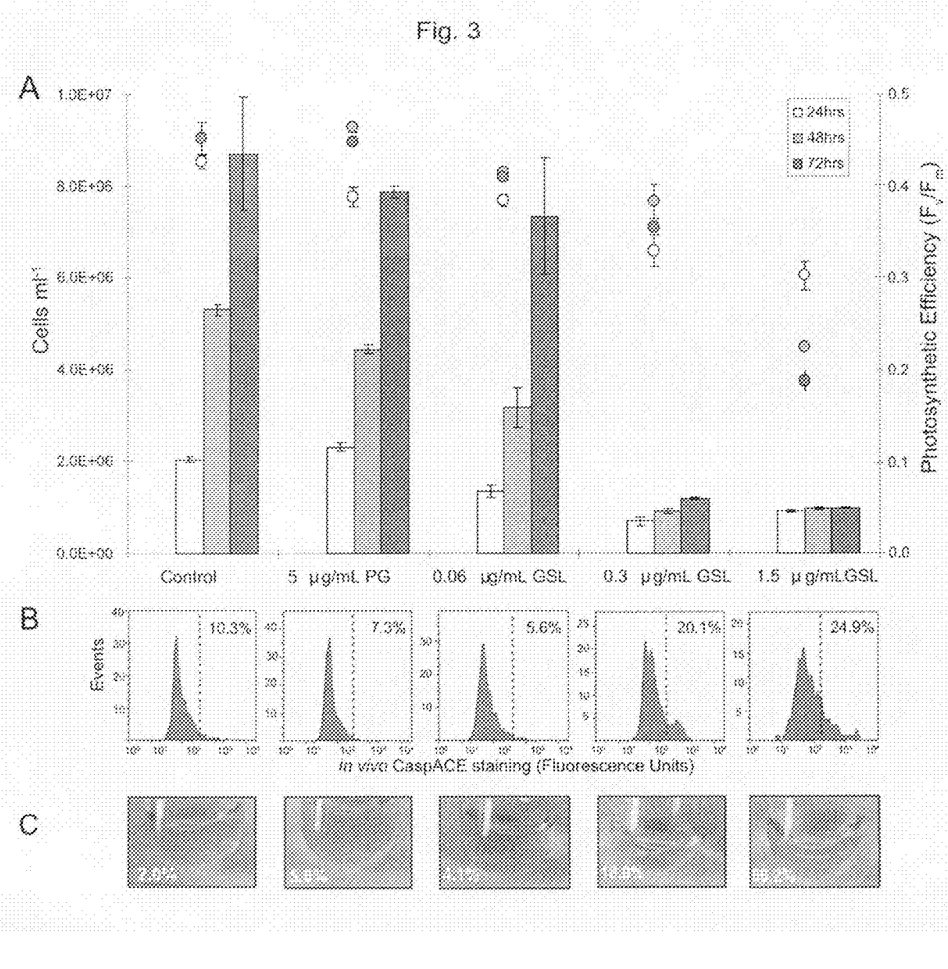

The strong correlation between the initiation of viral lysis, induction of caspase activity, and increase of viral GSLs, motivated us to examine their bioactive potential and ability to modulate host physiology over 72 h at various concentrations (0.06, 0.3, 1.5 µg/mL) (FIG. 3). We purified the viral GSLs from EhV86-infected Ehux374 cells by preparative HPLC. Their application had a remarkable effect on cell fate. They severely suppressed cell growth compared to control cells treated with DMSO (solvent) and control cells treated with phosphatidylglycerol (PG), which had a similar HPLC retention time (FIG. 3A). Cells treated with viral GSLs exhibited a dose-dependent induction of cell death above a distinct threshold concentration. Induction of cell death was accompanied by compromised photosynthetic efficiency (FIG. 3A, Fv/Fm) and the induction of in vivo caspase activity assessed through the cell staining with a fluorescently-labeled, broad spectrum caspase inhibitor, VAD-FMK-FITC (FIG. 3B and inset). Positive staining of Ehux374 cells was only observed for photosynthetic impaired cells, identified by their weak chlorophyll autofluorescence (data not shown). Approximately 20-25% of Ehux374 cells treated with 0.3 and 1.5 µh/ml GSLs had elevated caspase activity after 48 h, reaching up to 35% after 72 h (FIG. 3B). Likewise, up to 18% and 56.2% of the cells were SYTOX positive at 0.3 and 1.5 µg/mL GSLs, respectively (FIG. 3C), indicative of compromised cell membrane integrity late in the cell death cascade and consistent with findings of phytoplankton PCD triggered by abiotic stresses (Vardi et al., Curr. Biol. 9, 1061 (1999)). Less than 5.8-10.2% of cells were positively stained in the control treatments and in cells that were treated with a sub-lethal GSL concentration (e.g. 0.06 µg/mL), indicating low mortality in these cells. A visual comparison of control (DMSO, PG) and GSL treatments >0.06 µg/mL clearly revealed massive cell lysis in the latter (FIG. 3C). Notably, nearly identical cell death dynamics were observed between viral infection and cell death induced by application of purified, viral GSLs (compare FIG. 2A-C and FIG. 3).

Given their potent ability to trigger *E. huxleyi*'s PCD response in a dose-dependent manner and their presence in purified EhV virions, viral GSLs may be part of an elegant timing mechanism for viral release. In such a mechanism, host lysis is dependent on the accumulation of viral myristoyl GSLs to a critical effective concentration, above which host PCD is induced. According to our measurements, an EhV86 virion contains ~0.1-0.3 fg of myristoyl GSLs. At a typical burst size of ~800-1,000 viruses cell$^{-1}$ (Bidle et al., Proc.

Natl. Acad. Sci. USA. 104, 6049 (2007)), an effective intracellular concentration of ca. 100 fg cell$^{-1}$ is reached; this concentration is identical to the 100-200 fg cell$^{-1}$ we observed in host cells prior to lysis and is well within the critical threshold concentration for PCD activation (FIG. 2D). This strategy is also consistent with observations of low grade, persistent viral production during early phase infection prior to massive host cell lysis, when the accumulated, internal GSL concentration is too low to induce host PCD.

While not wishing to be bound by any theory, based on our measurements of the cellular production quotas of GSLs (100-200 fg cell$^{-1}$), we believe that such bioactive molecules have the potential to elicit cell death in surrounding, uninfected cells under natural bloom densities, and, hence, act as a bloom termination signal. It has been suggested that one potential evolutionary driver of PCD in unicellular organisms is a 'viral exclusion' strategy (Bidle et al., Proc. Natl. Acad. Sci. USA. 104, 6049 (2007)). At E. huxleyi bloom cell abundances (ca. 10,000 cells ml$^{-1}$), lysis may lead to sufficiently high local GSL concentrations sufficient to effectively compromise cell physiology and prevent viral infection through premature death of surrounding cells (see FIG. 3). Similar findings were recently reported for diatom-derived oxylipins found to act as infochemicals to either potentiate PCD or to induce resistance in sub-lethal doses (Vardi et al., Curr. Biol. 18, 895 (2008), Vardi et al., Plos Biology 4, 411 (2006).

Taken together, these observations demonstrated that viral GSLs have a critical role in inducing caspase activity and host PCD in a dose-dependent manner. These viral "toxins" can biomimic viral infection and induce PCD in uninfected E. huxleyi cells, a process that is essential for successful virus infection (Bidle et al., Proc. Natl. Acad. Sci. USA. 104, 6049 (2007)). In contrast, inhibition of caspase activity in infected Ehux374 cells severely impaired viral propagation, improved photosynthetic efficiency, and significantly prolonged host survival (Bidle et al., Proc. Natl. Acad. Sci. USA. 104, 6049 (2007)). Viral toxin analogs have also been found in cytoplasmic persisting double-stranded RNA viruses where three different 'killer toxins' induced caspase-mediated apoptosis in yeast (Reiter et al., J. Cell Biol. 168, 353 (2005)). GSLs have been specifically found to act as effective elicitors in a wide range of phytopathogens by inducing the accumulation of antimicrobial compounds (phytoalexins), cell death, and increased resistance to subsequent infection by compatible pathogens in rice plants (Koga et al., J. Biol. Chem. 273, 31985 (1998)). Elevated ceramide concentrations have also been implicated in modulation of endocytic pathways and lipid raft microdomain formation (Grassme et al., Nat Med 9, 322 (2003)). Consequently, ceramide enrichment of plasma membranes can serve to modulate entry, replication and release of viruses (Bragger et al., Proc. Natl. Acad. Sci. USA. 103, 2641 (2006), H. Sakamoto et al., Nat Chem Biol 1, 333 (2005)). GSL enrichment in an intact EhV86 virions and profound accumulation during lytic phase may suggest similar function.

Example 3

Host Resistance to Lytic Viral Infection

In contrast to PCD induced by viral glycosylated sphingolipids in sensitive strains of E. huxleyi, host resistance was characterized by the absence of toxic viral GSLs and caspase activity, both of which are required to induce PCD (FIG. 2). We detected unique lipids in resistant strains that were absent from susceptible strains, shedding insight into a potential molecular basis for viral resistance, aside from the induced sexual differentiation mechanism to evade viral infection.

Figure 4:
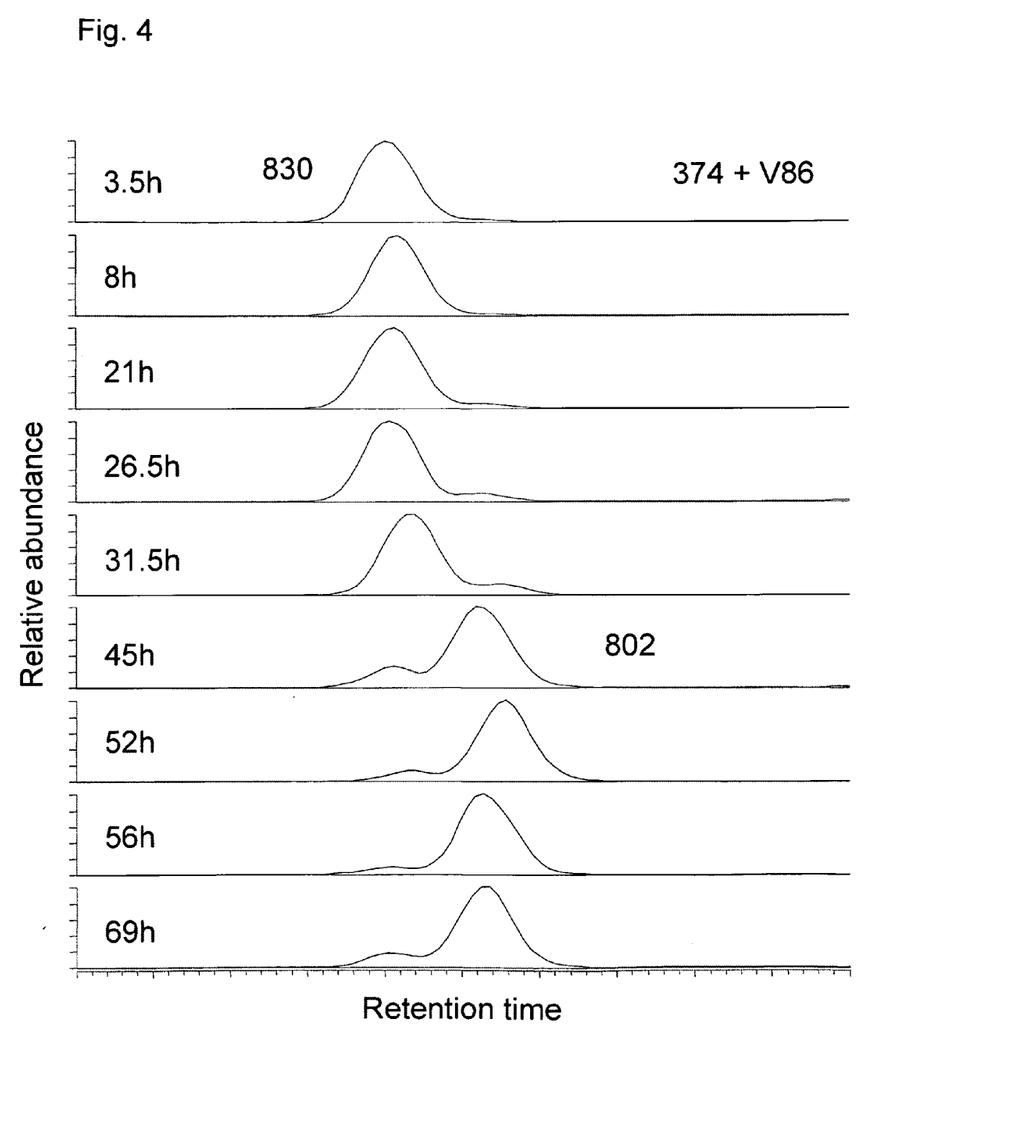
Figure 5:
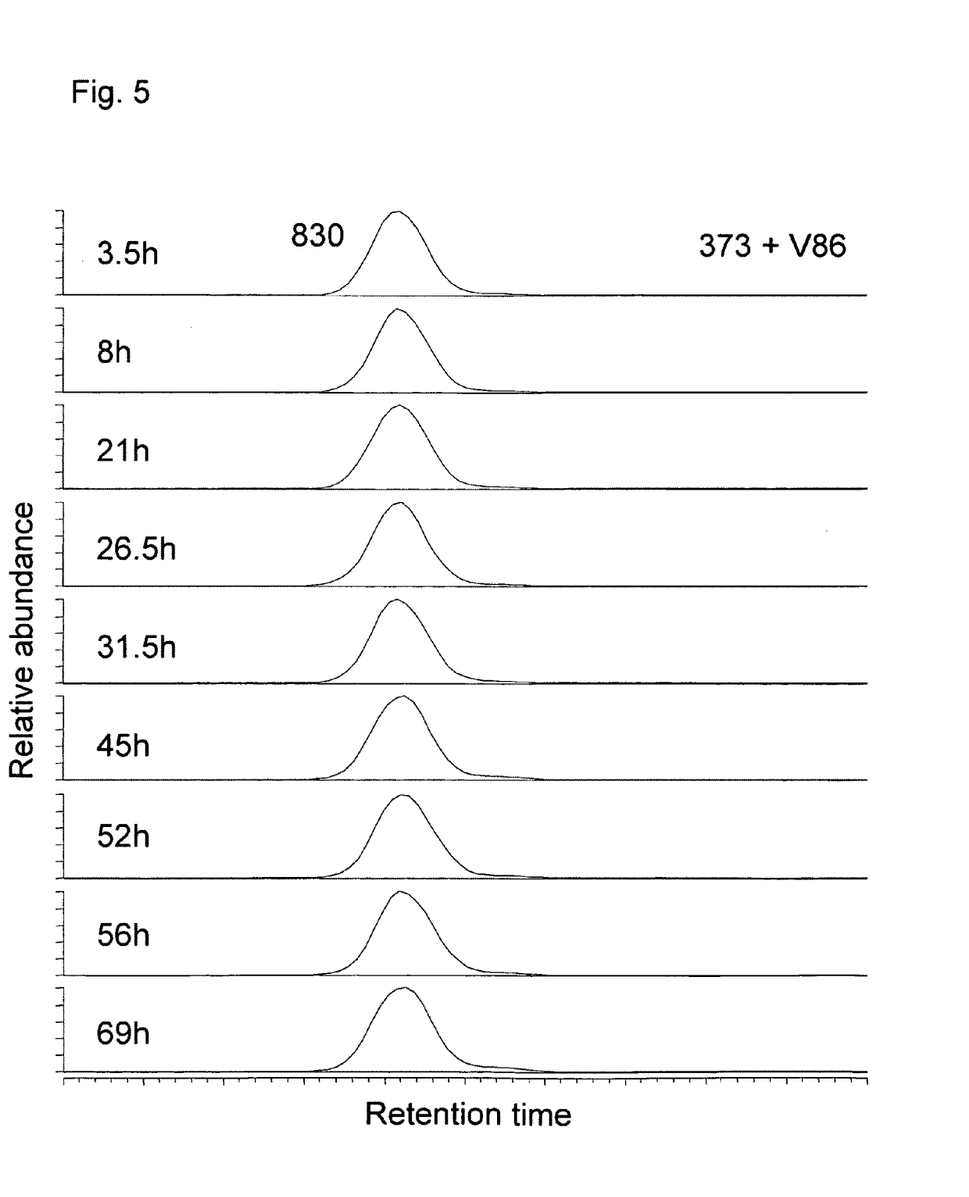
FIG. 5 shows the absence of induction of the 802 lipids in resistant strain Ehux373. The 802 lipids are not induced in resistant strain Ehux373 and levels of the 830 lipids remain constant.
Figure 6:
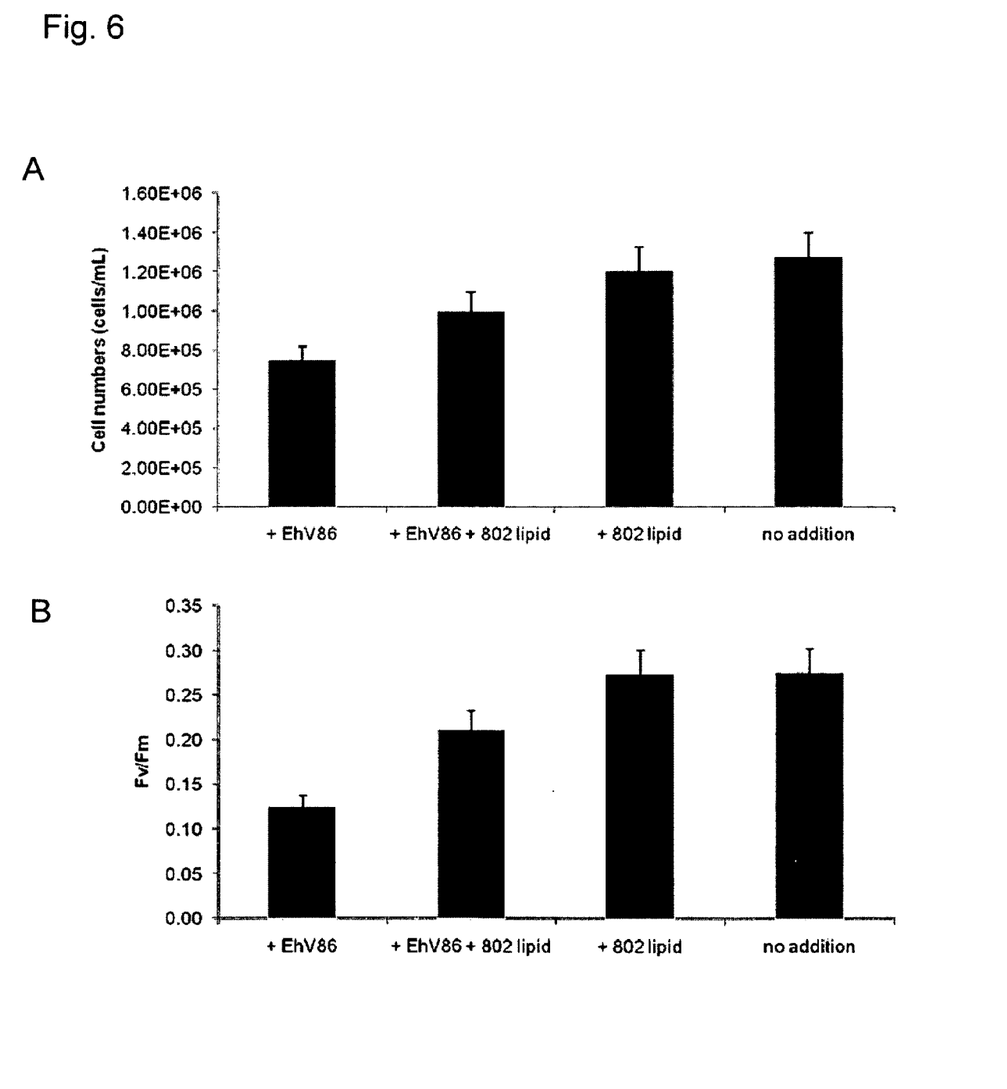
FIG. 6 summarizes survival data of Ehux374 after treatment with lipid 802. In measures of photosynthetic health and cell growth, the cells treated with a 1:1000 dilution of lipid 802 show prolonged survival after viral infection, relative to untreated controls.

We explored the abundance of the groups of other lipids (herein called 830 lipids and 802 lipids). Detailed profiles of these lipids are depicted in FIGS. 4 and 5 during the course of viral infection. A dramatic induction (>100 fold) of 802 is clearly observed only in sensitive strain Ehux374 during the onset of lytic phase (FIG. 4) and not by infected Ehux373 resistant strain (FIG. 5). Concomitant with the induction of 802, a major reduction in 830 occurred during the lytic phase. Preliminary data on the biological activity of 802 has revealed prolonged survival of more than 25% Ehux374 population during viral infection both in term of photosynthetic health (FIG. 6B) and cell growth (FIG. 6A). Hence, this compound may effectively protect host cells against successful viral infection, allowing a significant subpopulation to survive.

Material and Methods

Assessment of Cell Growth and Physiology

Emiliana huxleyi strains CCMP 373 and 374 were obtained from the Provasoli-Guillard Center for Culture of Marine Phytoplankton (CCMP) and batch grown in f/2 medium (minus Si) at 18° C., 14:10 (L:D) cycle and ≈150 µmol quanta m$^{-2}$·s$^{-1}$ with constant aeration. Cell abundance was determined by using a Coulter Multisizer II (Beckman Coulter, Fullerton, Calif.). Fluorescence Induction and Relaxation System (FIRe; Satlantic Instruments) was used to derive the maximum photochemical quantum yield of photosystem II (Fv/Fm), an indicator of photosynthetic health (Kolber et al., Biochim. Biophys. Acta 1367, 88 (1998)).

EhV86 Isolation

Viral particles were purified from a lysate of E. huxleyi CCMP strain 374 culture infected with EhV-86. Briefly, host cells were cultured in 10 liters of f/2 medium at 18° C. in 14 h: 10 h light-dark illumination. Exponentially growing (1.5× 10$^6$ cells ml$^{-1}$) cells were infected with fresh EhV-86 lysate. Once clearing of the host culture was observed (5 days later), the lysate was passed through a GF/F and 0.45 µm pore size Strivex filters; The filtrate was concentrated by tangential flow filtration (Vivaflow200, 50 kDa Sartorius) to 50 ml, according to manufacture instructions. Virus particles were purified by CsCl$_2$ gradient (1.1 g/ml, 1.2 g/ml, 1.3 g/ml, 1.4 g/ml) ultracentrifugation at 25000 rpm at 22° C. for 2 h in a SW41 Ti Beckman rotor. The virus band was removed with a syringe and filtered on a pre-combusted 0.02 µm Anodisc filter, and immediately frozen in liquid N$_2$ for lipid analysis. The presence of EhV86 virions in the purified viral fraction was verified by PCR amplification with specific capsid primers (Schroeder et al., Arch. Virol. 147, 1685 (2002)) and epifluorescence microscopy following SYBR Gold (Invitrogen) staining (Bidle et al., Proc. Natl. Acad. Sci. USA. 104, 6049 (2007)).

Measurement of Caspase Activity and Cell Death

Cells were pelleted via centrifugation, frozen immediately in liquid nitrogen, and stored at −80° C. until processing for subsequent biochemical analyses. Pellets were resuspended in caspase activity buffer (50 mM HEPES pH 7.3, 100 mM NaCl/10% sucrose/0.1% CHAPS/10 mM DTT) and sonicated. Cellular debris was pelleted by centrifugation (16,000 g; room temperature; 2 min) as described in (Bidle et al., Proc. Natl. Acad. Sci. USA. 104, 6049 (2007)). Cell extracts were incubated with 50 µM IETD-AFC (Calbiochem, San Diego, Calif.) for 4 h at 20° C. The hydrolysis of IETD-AFC was monitored by measuring the accumulation of the fluorescence in a Spectra Max Gemini XS plate reader (excitation 400 nm, emission 505 nm). In vivo caspase activity was assessed in E. huxleyi cells by direct staining with CaspACE FITC-VAD-FMK (Promega, Madison Wis.). Cells were pelleted by centrifugation, washed once with PBS (pH 7.5), and resuspended in PBS before the addition of CaspACE (final concentration, 20 μM). Cells were stained for 20 min at 18° C. in the dark, after which they were pelleted by centrifugation, washed once with PBS, fixed with 2% formalin/PBS, and stored at 4° C. until analyzed. Cells were visualized by epifluorescence microscopy using an Olympus IX71 inverted microscope and analyzed for percentage of positive cells at 520 nm using an InFlux Model 209S Mariner flow cytometer and high-speed cell sorter (BD Biosciences). DMSO-treated cells served as controls and were used to gate negatively stained E. huxleyi cells, since viral myristoyl GSLs were reconstituted in DMSO. Cell death was also determined by assaying the plasma membrane integrity with SYTOX Green (Invitrogen), a fluorescent DNA-binding dye that is excluded from viable cells. After 15 minutes of incubation with 1 μM SYTOX in the dark, cells were washed with filtered seawater, quantified by screening 400-600 cells via epifluorescence microscopy (FITC filter; 480 nm excitation and 525 nm emission).

Transmission Electron Microscopy (TEM)

Cells were pelleted, washed with 0.2-μm filtered seawater, and preserved in Trump's EM fixative (4% formaldehyde/1% glutaraldehyde in phosphate buffer, pH 7.2) for at least 4 h at 4° C. Fixed cells were rinsed three times in Milloning's phosphate buffer, pH7.3, postfixed for 2 h in 1% buffered $OsO_4$, washed three times, and dehydrated through a graded series of ethanol. After replacement of ethanol with propylene oxide, cells were embedded in Epon-Araldite mixture. Sections were cut by using a LKB 2088 ultramicrotome, collected on 200-mesh copper grids, and stained with uranyl acetate and lead citrate. The stained sections were photographed in a JEM-100CXII electron microscope.

Lipid Analysis

E. huxleyi cells were collected by filtration on precombusted GF/F filters, which were snap frozen in liquid nitrogen. Subsequently, lipids were extracted using a modified Bligh Dyer method, as described (Van Mooy et al., Proc. Natl. Acad. Sci. USA 103, 8607 (2006)). Cellular polar membrane lipids were analyzed by HPLC/ESI-MS as described (Sturt et al. Rapid Comm. Mass Spectrom. 18, 617 (2004)) using an Agilent 1100 HPLC and Thermo Finnigan LCQ Deca XP ion-trap mass spectrometer. Authentic glycosphingolipid standards (Avanti Polar Lipids, brain cerebrosides) were used for initial identification of retention times and to identify characteristic $MS^2$ and $MS^3$ fragmentation; these authentic standards were also used to construct standard curves for quantification. A subset of the samples were analyzed using identical HPLC and ESI conditions on a Thermo FTQ high-resolution Fourier-transform ion cyclotron resonance mass spectrometer (FT-MS) for confirmation of elemental formulas in glycosphingolipid molecular ions and $MS^2$ fragment ions.

Incorporation By Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

References

Allen, J. Virology, 80(15) 7699-7705 (2006)
Allen et al., Environmental Microbiology, 9(4) 971-982 (2007)
Allen et al., Proteome Sci. 6 (2008)
Bidle and Falkowski. Nature Rev. Microbiol. 2:643-655 (2004)
Bidle et al., PNAS 104(14): 6049-6054 (2007)
Bidle and Bender, Eukaryotic Cell 7:223-236 (2008)
Brügger et al., Proc. Natl. Acad. Sci. USA. 103, 2641 (2006)
Brussard, J. Eukaryotic Microbiology, 51:2, 125-138, (2004)
Brussard, Aquat. Microb. Ecol., 10:105-113, (1996)
Douglas et al., Journal of Immunological Methods 188, 219-228 (1995)
Elstein and Zucker, Experimental Cell Research 211, 322-331 (1994)
Fuhrman, Nature 399:541-548 (1999)
Grassme et al., Nat Med 9, 322 (2003)
Leist et al., The Journal of Immunology 153, 1778-1788 (1994)
Lynch and Dunn, New Phytol. 161, 677 (2004)
Khuruna et al., Current Science, 88 (5) 740-752 (2005)
Koga et al., J. Biol. Chem. 273, 31985 (1998)
Kolber et al., Biochim. Biophys. Acta 1367, 88 (1998)
Koopman et al., Blood 84, 5, 1415-1420 (1994)
Parker et al., Ann. Rev. Genet. 42:619-45 (2008)
Reiter et al., J. Cell Biol. 168, 353 (2005)
Sakamoto et al., Nat Chem Biol 1, 333 (2005)
Schroeder et al., Arch. Virol. 147, 1685 (2002)
Sturt et al. Rapid Comm. Mass Spectrom. 18, 617 (2004)
Suttle, Nature Reviews Microbiology, Vol. 5, 801-812 (2007)
Suzan-Monti et al., PLoS ONE 2, e328 (2007)
Van Mooy et al., Proc. Natl. Acad. Sci. USA 103, 8607 (2006)
Van Mooy et al., Nature, 458: 69-72, (2009)
Vardi et al., Curr. Biol. 9, 1061 (1999)
Vardi et al., Plos Biology 4, 411 (2006)
Vardi et al., Curr. Biol. 18, 895 (2008)
Verhaegen et al., European Microscopy and Analysis (1998)
Wilson et al., Science 209, 1090 (2005)

We claim:

1. A method for identifying one or more apoptosis-inducing glycosylated sphingolipids, comprising:
   (a) obtaining a sample of one or more glycosylated sphingolipids from a virally-infected phytoplankton;
   (b) contacting a target cell with the sample;
   (c) assaying the target cell for apoptosis-associated activity in the presence of the sample;
   wherein apoptosis-associated activity in the target cell indicates that the sample comprises one or more apoptosis-inducing glycosylated sphingolipids.

2. The method of claim 1, wherein the phytoplankton are coccolithophores.

3. The method of claim 2, wherein the coccolithophores are E. huxleyi.

4. The method of claim 1, wherein the virus is a coccolithovirus.

5. The method of claim 4, wherein the coccolithovirus is EhV86.

6. The method of claim 1, further comprising isolating the one or more apoptosis-inhibiting glycosylated sphingolipids from the sample.

7. The method of claim 1, wherein the target cell is a prokaryotic cell.

8. The method of claim 1, wherein the target cell is a eukaryotic cell.

9. A method of manufacturing one or more glycosylated sphingolipids, comprising:
   (a) infecting phytoplankton with a virus;
   (b) culturing the infected phytoplankton; and
   (c) isolating the one or more glycosylated sphingolipids from the infected phytoplankton.

10. The method of claim 9, wherein the one or more glycosylated sphingolipids are apoptosis-inducing glycosylated sphingolipids.

11. A method for identifying one or more glycerolipids capable of inhibiting viral-mediated apoptosis, comprising:
    (a) obtaining a sample of one or more glycerolipids from a virally-infected phytoplankton;
    (b) contacting a target cell with the sample; and
    (c) assaying the target cell for apoptosis-associated activity in the presence of the sample and further in the presence of a virus that induces apoptosis in the target cell in the absence of the sample;
    wherein a decrease in apoptosis-associated activity in the target cell relative to the apoptosis-associated activity in the absence of the sample indicates that the sample comprises one or more glycerolipids capable of inhibiting viral-mediated apoptosis.

12. The method of claim 11, wherein the phytoplankton are coccolithophores.

13. The method of claim 12, wherein the coccolithophores are *E. huxleyi*.

14. The method of claim 11, wherein the virus is a coccolithovirus.

15. The method of claim 14, wherein the coccolithovirus is EhV86.

16. The method of claim 11, further comprising isolating the one or more glycerolipids from the sample.

17. The method of claim 11, wherein the target cell is a prokaryotic cell.

18. The method of claim 11, wherein the target cell is a eukaryotic cell.

* * * * *